(12) United States Patent
Hotter et al.

(10) Patent No.: US 9,510,925 B2
(45) Date of Patent: Dec. 6, 2016

(54) SURGICAL MESHES

(75) Inventors: Joseph Hotter, Lyons (FR); Jon Reinprecht, Watertown, CT (US); Norman Aminuddin, Madison, CT (US); Jonathan Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 1214 days.

(21) Appl. No.: 12/986,203

(22) Filed: Jan. 7, 2011

(65) Prior Publication Data

US 2011/0190795 A1 Aug. 4, 2011

Related U.S. Application Data

(60) Provisional application No. 61/300,532, filed on Feb. 2, 2010.

(51) Int. Cl.
*A61B 17/08* (2006.01)
*A61F 2/00* (2006.01)

(52) U.S. Cl.
CPC ...... *A61F 2/0063* (2013.01); *A61F 2002/0068* (2013.01); *A61F 2250/005* (2013.01); *A61F 2250/0017* (2013.01); *A61F 2250/0019* (2013.01); *A61F 2250/0031* (2013.01)

(58) Field of Classification Search
CPC ............ A61F 2/0063; A61F 2002/0068; A61F 2250/0014; A61F 2250/0017; A61F 2250/0019; A61F 2250/0031
USPC .. 606/151, 154; 424/426; 427/2.31; 623/1.5, 1.51, 1.54, 23.74, 23.75; 602/76; 442/2, 3, 4, 5, 164, 199, 203, 220, 287, 442/290, 304, 312, 313, 314; 428/105, 107, 428/114, 115, 196, 197, 373, 902
See application file for complete search history.

(56) References Cited

U.S. PATENT DOCUMENTS

| | | | |
|---|---|---|---|
| 5,711,960 A * | 1/1998 | Shikinami | 424/426 |
| 7,582,576 B2 | 9/2009 | Snijder et al. | |
| 2004/0009731 A1* | 1/2004 | Rabinowicz | 442/316 |
| 2005/0288797 A1 | 12/2005 | Howland | |
| 2006/0014459 A1* | 1/2006 | Snijder et al. | 442/304 |
| 2006/0200169 A1 | 9/2006 | Sniffin | |
| 2006/0200170 A1 | 9/2006 | Aranyi | |
| 2006/0229640 A1 | 10/2006 | Whitfield | |
| 2010/0189764 A1 | 7/2010 | Thomas et al. | |

FOREIGN PATENT DOCUMENTS

| | | | | |
|---|---|---|---|---|
| EP | 0523743 | * | 4/1996 | ............ A61L 17/00 |
| WO | WO 2005/094721 A1 | | 10/2005 | |
| WO | WO 2006/071023 A1 | | 7/2006 | |
| WO | WO2006102374 | * | 9/2006 | ............ A61F 13/15 |

OTHER PUBLICATIONS

European Search Report for EP 11250108.5-1257 date of completion is May 18, 2011 (3 pages).

* cited by examiner

*Primary Examiner* — Robert Lynch (57) ABSTRACT

An implant includes a central portion composed of at least one yarn interconnected to form openings therein and a peripheral portion extending around the central portion. The peripheral portion includes at least one high strength yarn.

23 Claims, 4 Drawing Sheets

SURGICAL MESHES

CROSS-REFERENCE TO RELATED APPLICATIONS

This application claims the benefit of, and priority to, U.S. Provisional Application No. 61/300,532, filed on Feb. 2, 2010, the entire disclosure of which is incorporated by reference herein.

BACKGROUND

Technical Field

The present disclosure relates to surgical meshes, and more particularly, to surgical meshes reinforced with high strength fibers to mitigate tear propagation and mesh failure.

Background of Related Art

Techniques for repairing damaged or diseased tissue are widespread in medicine. Wound closure devices, such as sutures and staples, as well as other repair devices like mesh or patch reinforcements, are frequently used for repair. For example, in the case of hernias, techniques involving the use of a mesh or patch to reinforce the abdominal wall are used. The mesh or patch is generally soft and pliant in order to conform to the abdominal wall and flex with movement of the abdominal wall. The mesh or patch may be held in place by suturing or stapling to the surrounding tissue.

During a hernia repair procedure, post surgical complications may arise. For example, a linear tear may form along either the warp or weft direction of a surgical mesh thereby causing mesh failure at the repaired hernia opening. In another example, fibers of a surgical mesh may break at the suture/mesh interface around the periphery of the surgical mesh thereby reducing the security of the mesh at the abdominal wall. This may cause the mesh to peel away from the abdominal wall thereby compromising the surgical repair of the hernia defect.

It would be advantageous to provide a soft, pliant surgical mesh that is reinforced to prevent mesh failure.

SUMMARY

An implant of the present disclosure includes a central portion surrounded by a peripheral portion. The central portion is composed of at least one yarn that is interconnected to form openings therein. The peripheral portion includes at least one high strength yarn. In embodiments, the at least one yarn of the central portion is interconnected via one of knitting, weaving, and combinations thereof. In some embodiments, the at least one yarn of the central portion is interconnected via warp knitting or weaving. The central portion may include at least two yarns, at least one yarn being a primary yarn and at least one yarn being a high strength yarn.

In some embodiments, the high strength yarn of the implant may have a tensile strength of at least 1 Gpa. In other embodiments, the tensile strength of the high strength yarn is at least 2 times that of the primary yarns, in embodiments, high strength yarns have a tensile strength that is about 5 times that of the primary yarns, and in yet other embodiments, high strength yarns have a tensile strength that is over 10 times that of the primary yarns.

The tensile strength of the peripheral portion is greater than the tensile strength of the central portion. In embodiments, the peripheral portion has a tensile strength that is at least 50% greater than a tensile strength of the central portion. In some embodiments, the tensile strength of the peripheral portion is about 100% greater than the tensile strength of the central portion, and in other embodiments, the tensile strength of the peripheral portion is about 200% greater than the tensile strength of the central portion.

The at least one yarn of the central portion may extend at least partially into the peripheral portion of the implant, in some embodiments, throughout the peripheral portion of the implant. In such embodiments, the at least one high strength yarn is intermingled with the at least one yarn in the peripheral portion of the implant via one of knitting, weaving, sewing, embroidering, and combinations thereof. In some embodiments, a terminal edge may be fanned around the implant formed solely of the at least one high strength yarn. The terminal edge may be formed via one of knitting, weaving, and combinations thereof.

The peripheral portion may also be solely formed from the at least one high strength yarn. In embodiments, the at least one high strength yarn is interconnected to the central portion via one of knitting, weaving, and combinations thereof. In some embodiments, the at least one high strength yarn is interconnected via welt knitting or weaving in the warp and weft directions.

The at least one yarn of the central portion may include at least one bi-component fiber. In embodiments, the bi-component fiber includes a non-absorbable core and an absorbable sheath surrounding the non-absorbable core.

The at least one high strength yarn may be a monofilament or a multifilament yarn. In embodiments, the high strength yarn may be composed of ultra high molecular weight polyethylene. In other embodiments, the high strength yarn may be composed of high molecular weight polyethylene terephthalate. The at least one high strength yarn may include at least one bi-component fiber. In embodiments, the bi-component fiber includes a non-absorbable core and a non-absorbable sheath surrounding the non-absorbable core. In some embodiments, the non-absorbable core and/or non-absorbable sheath is ultra high molecular weight polyethylene.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF THE EMBODIMENTS

Surgical meshes in accordance with the present disclosure are fabricated from a textile including a central, or inner, portion of yarns interconnected and bound by a peripheral, or outer, portion of yarns including at least one high strength fiber. The central portion provides the primary structure to the implant while the peripheral portion makes the implant resistant to failure. Mesh failure includes such things as tearing and tear propagation, breakage of fibers or yarns, separation at the suture/mesh interface, among other defects which can compromise the integrity of the mesh. While the surgical meshes are especially suitable for surgical repair of hernias, it is envisioned that the meshes can be used in connection with other surgical procedures requiring repair of soft tissue defects such as muscle or wall tissue defects, pelvic organ prolapse, urinary incontinence, sports surgery, and orthopedic applications, for example. The meshes of the present disclosure can be in the form of sheets, patches, slings, suspenders, and other implants and composite materials such as pledgets, buttresses, wound dressings, drug delivery devices, and the like.

Yarns forming the surgical mesh may be monofilament or multifilament yarns which may be made of any suitable biocompatible material. Suitable materials from which the mesh can be made should have the following characteristics: sufficient tensile strength to support a fascial wall during repair of a defect in the fascial wall causing a hernia; sufficiently inert to avoid foreign body reactions when retained in the body for long periods of time; easily sterilized to prevent the introduction of infection when the mesh is implanted in the body; and suitably easy handling characteristics for placement in the desired location in the body. The mesh should be sufficiently pliable to conform to a fascial wall and flex with movement of the wall, while being sufficiently rigid to retain its mesh shape. The mesh should also be sufficiently strong to avoid tearing of portions thereof, including the portion through which surgical fasteners are applied to affix the mesh to tissue.

In some embodiments, the yarns include at least two filaments which may be arranged to create openings therebetween, the yarns also being arranged relative to each other to form openings in the mesh. Alternatively, the mesh may be formed from a continuous yarn that is arranged in loops that give rise to the openings in the mesh. The use of a mesh having yarns spaced apart in accordance with the present disclosure has the advantage of reducing the foreign body mass that is implanted in the body, while maintaining sufficient tensile strength to securely support the defect and tissue being repaired by the mesh. Moreover, the openings of the mesh of the present disclosure may be sized to permit fibroblast proliferation and in-growth and ordered collagen laydown, resulting in integration of the mesh into the body. Thus, the spacing between the yarns may vary depending on the surgical application and desired implant characteristics as envisioned by those skilled in the art. Moreover, due to the variety of sizes of defects, and of the various fascia that may need repair, the mesh may be of any suitable size.

The yarns may be braided, twisted, aligned, fused, or otherwise joined to form a variety of different mesh shapes. In embodiments in which at least two filaments form a yarn, the filaments may be drawn, oriented, crinkled, twisted, braided, commingled or air entangled to form the yarn. The yarns may be woven, knitted, interlaced, braided, or formed into a surgical mesh by non-woven techniques. The structure of the mesh will vary depending upon the assembling technique utilized to form the mesh, as well as other factors such as the type of fibers used, the tension at which the yarns are held, and the mechanical properties required of the mesh.

In embodiments, knitting may be utilized to form a mesh of the present disclosure. Knitting involves, in embodiments, the intermeshing of yarns to form loops or interlooping of the yarns. In some embodiments, yarns may be warp-knitted thereby creating vertical interlocking loop chains and/or may be weft-knitted thereby creating rows of interlocking loop stitches across the mesh. In other embodiments, weaving may be utilized to form a mesh of the present disclosure. Weaving may include, in embodiments, the intersection of two sets of straight yarns, warp and weft, which cross and interweave at right angles to each other, or the interlacing of two yarns at right angles to each other. In some embodiments, the yarns may be arranged to form a net mesh which has isotropic or near isotropic tensile strength and elasticity.

In embodiments, the yarns may be nonwoven and formed by mechanically, chemically, or thermally bonding the yarns into a sheet or web in a random or systematic arrangement. For example, yarns may be mechanically bound by entangling the yarns to form the mesh by means other than knitting or weaving, such as matting, pressing, stitch-bonding, needlepunching, or otherwise interlocking the yarns to form a binderless network. In other embodiments, the yarns of the mesh may be chemically bound by use of an adhesive, such as a hot melt adhesive, or thermally bound by applying a binder, such as a powder, paste, or melt, and melting the binder on the sheet or web of yarns.

The yarns may be fabricated from any biodegradable and/or non-biodegradable polymer that can be used in surgical procedures. The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. Absorbable materials are absorbed by biological tissues and disappear in vivo at the end of a given period, which can vary for example from hours to several months, depending on the chemical nature of the material. It should be understood that such materials include natural, synthetic, bioabsorbable, and/or certain non-absorbable materials, as well as combinations thereof.

Representative natural biodegradable polymers include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups include, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein, and copolymers and blends thereof; alone or in combination with synthetic polymers.

Synthetically modified natural polymers which may be used to form the yarns include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt.

Representative synthetic biodegradable polymers which may be utilized to form yarns include polyhydroxy acids prepared from lactone monomers such as glycolide, lactide, caprolactone, ε-caprolactone, valerolactone, and δ-valerolactone, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

Synthetic degradable polymers also include hydrophilic vinyl polymers expanded to include phosphoryl choline such as 2-methacryloyloxyethyl phosphorylcholine, hydroxamates, vinyl furanones and their copolymers, and quaternary ammonia; as well as various alkylene oxide copolymers in combination with other polymers such as lactones, orthoesters, and hydroxybutyrates, for example.

Rapidly bioerodible polymers, such as poly(lactide-co-glycolide)s, polyanhydrides, and polyorthoesters, which have carboxylic groups exposed on the external surface as the surface of the polymer erodes, may also be used.

Other biodegradable polymers include polyphosphazenes; polypropylene fumarates; polyimides; polymer drugs such as polyamines; perfluoroalkoxy polymers; fluorinated ethylene/propylene copolymers; PEG-lactone copolymers; PEG-polyorthoester copolymers; blends and combinations thereof.

Some non-limiting examples of suitable non-degradable materials from which the mesh may be made include polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

In certain embodiments, high strength yarns of the present disclosure may be composed of high molecular weight polyethylene terephthalate or ultra high molecular weight polyethylene.

Figure 1:
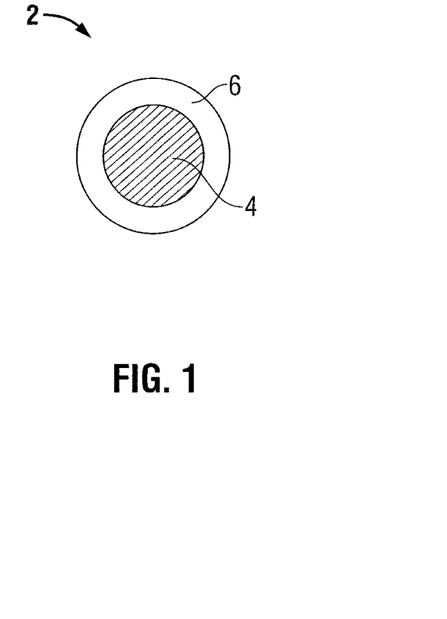
FIG. 1 is a cross-sectional view of an embodiment of a bi-component fiber of a surgical mesh in accordance with the present disclosure.

Yarns in accordance with the present disclosure may include one or more bi-component fibers. A bi-component fiber is a fiber composed of two polymers which may have different chemical and/or physical properties. As illustrated in FIG. 1, bi-component fiber 2 includes a core polymer 4 and a sheath polymer 6. Core polymer 4 may be fabricated from a non-absorbable or long lasting absorbable material and sheath polymer 6 may be fabricated from either a non-absorbable or absorbable material, such as one listed above.

Figure 2:
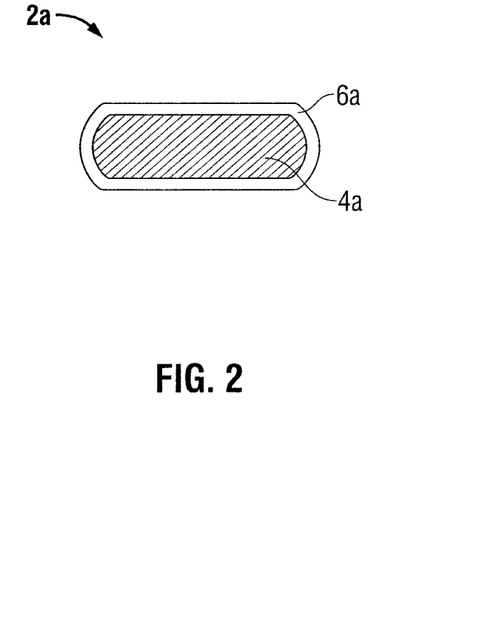
FIG. 2 is a cross-sectional view of another embodiment of a bi-component fiber of a surgical mesh in accordance with the present disclosure.
Figure 3:
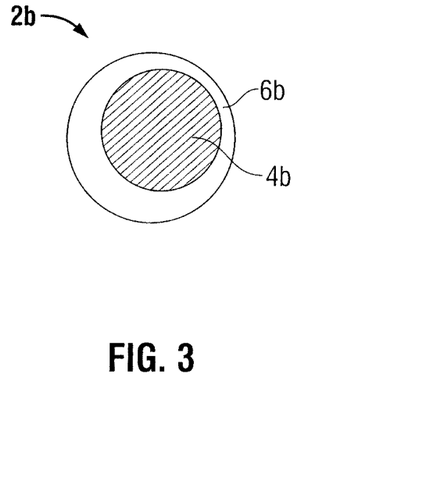
FIG. 3 is a cross-sectional view of yet another embodiment of a bi-component fiber of a surgical mesh in accordance with the present disclosure.

Bi-component fiber 2 may be a monofilament fiber which is co-extruded from two distinct polymers to exhibit a concentric sheath-core arrangement as illustrated in the current embodiment. Fiber 2 has a round cross-sectional shape including a core polymer 4 surrounded by a sheath polymer 6, the core polymer 4 and sheath polymer 6 both having a common center. Other cross-sectional shapes are envisioned, such as a flat cross-sectional shape as illustrated by fiber 2a, which includes core polymer 4a and sheath polymer 6a, in FIG. 2, as well as other modified cross-sections which may be co-extruded to generate fibers with more complex profiles as envisioned by those skilled in the art. As illustrated in FIG. 3, bi-component fiber 2b may also exhibit an eccentric sheath-core arrangement. Fiber 2b includes an off-center core polymer 4b surrounded by sheath polymer 6b.

Figure 4:
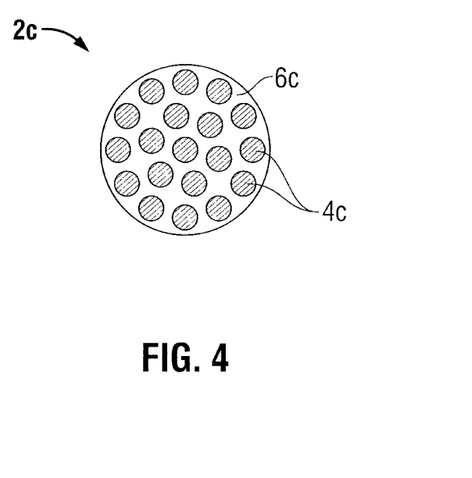
FIG. 4 is a cross-sectional view of another embodiment of a bi-component fiber of a surgical mesh in accordance with the present disclosure.

As illustrated in FIG. 4, bi-component fiber 2c may also be multifilament fibers which are spun and processed from microdenier filaments of core polymer 4c. Fiber 2c exhibits an islands-in-the-sea arrangement where two or more "islands," or core polymer filaments 4c are surrounded by a "sea," or sheath polymer 6c. This arrangement may provide for very fine strands of island polymer filaments 4c to be effectively handled by manufacturing equipment to spin and form fiber 2c. Core polymer filaments 4c may be arranged so as to be generally non-intersecting along their length. Although not necessarily parallel, core polymer filaments 4c may be generally free from entanglement or interlacing over a substantial portion of their length. Alternatively, core polymer filaments 4c may be woven, braided, or entangled by various processes within the purview of those skilled in the art. The core polymer filaments 4c may be spun inside the sheath polymer 6c. In embodiments, as little as about three and as many as about fifty or more core polymer filaments 4c may be handled effectively to form a single fiber 2c.

The sheath polymer may be applied to the core polymer of the bi-component fiber by any means within the purview of those skilled in the art including: extrusion; co-extrusion; pultrusion; gel spinning with one of the aforementioned processes; melt coating; spray coating; ultrasonic spray coating; electrostatic coating; powder coating; solvent/immersion coating such as dipping; spraying; solvent evaporation; sheath heat crimping; chemical surface modification; combinations thereof, and the like. In embodiments, powder coating may be accomplished by coating a dry form of polymer particles and melting them to form a conformal coating. In other embodiments, the sheath polymer may be applied to the core polymer by chemical surface modification which may include energy based polymerization such as ultraviolet, gamma, heat and/or chemical initiated processes, or by e-beam polymerization which may include polymerizing degradable polymers in the presence of the polymer utilized to form the core. Where applied as a coating, the sheath polymer may be in a solution including a biocompatible solvent such as hexafluoroisopropanol, acetone, isopropanol, methylene chloride, chloroform, combinations thereof, and the like.

In embodiments, the surface of the core polymer may include some degree of porosity to help anchor or impregnate at least a portion of the sheath polymer into the core. The porosity of the core polymer may also provide for tissue ingrowth following degradation/absorption of the sheath polymer. In embodiments, porosity is achieved by roughening the surface of the core polymer. Alternatively, the core polymer may maintain a smooth, non-porous surface such that the core and sheath polymers show little or no adhesion to each other.

In embodiments, the bi-component fibers may include a nonabsorbable or long lasting absorbable core and a shorter lasting absorbable sheath. The absorbable sheath may provide stiffness and rigidity to the mesh for ease of implantation and degrades to leave a pliant, flexible core for long-term implantation in the body. The sheath of the bi-component fiber may be absorbed by the body within a number of hours, such that only the core portion is left in the body for an extended period of time, typically for a long enough period of time to enable tissue ingrowth. The absorbable portion may be a rapidly bioerodible polymer or other fast absorbing polymer, as described above, having a fast degradation rate of just a few hours to less than an hour. In other embodiments, the absorbable portion may be absorbed from about 2 days to about 180 days post-implantation.

In embodiments in which the sheath polymer of the bi-component fiber is absorbable, the sheath polymer is generally thin for rapid degradation, thus, a large majority of the cross-section of the fiber is the core polymer. In some embodiments, the core polymer is about 65% to about 95% of the cross-section of the fiber, in other embodiments from about 70% to about 90%, and in yet other embodiments about 80%.

In embodiments, the absorbable sheath of the bi-component fiber provides stiffness to the entire bi-component fiber and thereby provides stiffness to the mesh as a whole. In other embodiments, the absorbable sheath exhibits stiffness such that, when the surgical mesh is folded, the mesh may spontaneously unfold to its original geometric shape. In yet another embodiment, the absorbable sheath of the bi-component fiber allows the surgical mesh to re-form into its original geometric shape following transport through a laparoscopic device into a body cavity.

Bioactive agents may be added to a surgical mesh of the present disclosure. A "bioactive agent" as used herein, is used in its broadest sense and includes any substance or mixture of substances that have clinical use. Consequently, bioactive agents may or may not have pharmacological activity per se, e.g., a dye. Alternatively, a bioactive agent could be any agent which provides a therapeutic or prophylactic effect; a compound that affects or participates in tissue growth, cell growth and/or cell differentiation; a compound that may be able to invoke or prevent a biological action such as an immune response; or a compound that could play any other role in one or more biological processes. A variety of bioactive agents may be incorporated into the mesh. Moreover, any agent which may enhance tissue repair, limit the risk of sepsis, and modulate the mechanical properties of the mesh (e.g., the swelling rate in water, tensile strength, etc.) may be added during the preparation of the filaments and/or the mesh or may be coated on or into the openings of the mesh.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Other bioactive agents which may be in the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present disclosure include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, (α-IFN and γ-IFN)); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; protein agonists; nucleic acids such as antisense molecules, DNA, and RNA; oligonucleotides; and ribozymes.

In some embodiments, a bioactive coating may be applied to the mesh as a composition or coating containing one or more bioactive agents, or bioactive agent(s) dispersed in a suitable biocompatible solvent. Suitable solvents for particular bioactive agents are within the purview of those skilled in the art.

In embodiments utilizing bi-component fibers, the bi-component fiber may be used for both forming the mesh of the present disclosure as well as for delivering a bioactive agent. Thus, in some embodiments, at least one bioactive agent may be combined or separately applied to the individual bi-component fibers of the mesh as a coating for quick release of the bioactive agent, to the sheath of the bi-component fibers for release during degradation if the sheath is absorbable, and/or to the core for long-term release over time. For example, the bioactive agents may be freely admixed with the polymers forming the core or sheath of the bi-component fiber or may be tethered to the polymers through any suitable chemical bonds.

Any coating composition containing the bioactive agent may encapsulate an entire fiber or yarn. Alternatively, the bioactive coating may be applied to one or more sides of a fiber or yarn. Such a coating will improve the desired therapeutic characteristics of the mesh.

The bioactive agent may be applied to the mesh utilizing any suitable method known to those skilled in the art. Some examples include, but are not limited to, spraying, dipping, layering, calendaring, etc. The bioactive agent may also be otherwise incorporated or applied to the mesh.

The central portion of the mesh may include primary yarns fabricated with any of the above listed materials interconnected in any manner described above. In some embodiments, the central portion may include primary yarns and one or more high strength yarns. The peripheral portion of the mesh includes at least one high strength yarn which may be used alone or in combination with any of the primary yarns of the central portion. The peripheral portion may be interconnected in the same, or in a different, way than the primary yarns of the central portion.

The high strength yarns are stronger than the primary yarns used to construct the bulk of the mesh. In embodiments, the high strength yarns may be dyed to contrast in color with the primary yarns of the mesh to aid the surgeon in identifying the high strength yarns. For example, visualization of the high strength yarns may aid in the proper placement of surgical fasteners for fixation of the mesh to tissue. In addition visualization of the yarns may aid the surgeon in orienting and properly placing the mesh over the target tissue.

A high strength yarn may be a monofilament or multifilament yarn fabricated from any absorbable or nonabsorbable material described above having a tensile strength of at least 1.0 Gpa. In embodiments, the high strength yarn is ultra high molecular weight polyethylene, used alone or in combination with other polymer filaments. High strength yarns may be characterized as having a tensile strength that is at least 2 times that of the primary yarns, in embodiments, high strength yarns have a tensile strength that is about 5 times that of the primary yarns, and in yet other embodiments, high strength yarns have a tensile strength that is over 10 times that of the primary yarns.

Accordingly, the tensile strength of the peripheral portion containing the high strength yarns will be greater than the tensile strength of the central portion containing the primary yarns. Thus, the peripheral portion of the mesh is more resistant to failure compared to the central portion of the mesh. The tensile strength of the peripheral portion is at least 10% greater than the tensile strength of the central portion. In embodiments, the tensile strength of the peripheral portion is about 50% greater than the tensile strength of the central portion, in other embodiments, the tensile strength of the peripheral portion is about 100% greater than the tensile strength of the central portion, and in yet other embodiments, the tensile strength of the peripheral portion is about 200% greater than the tensile strength of the central portion.

The high strength yarns may include one or more bi-component fibers, alone or in combination with other polymeric filaments. In embodiments, the bi-component fibers of the high strength yarns may include a nonabsorbable core and a nonabsorbable sheath. In embodiments, the weight ratio between the sheath and core is about 5:1, in other embodiments, the ratio is about 3:1, and in yet other embodiments, the ratio is less than 2:1. An example of a nonabsorbable bi-component yarn which may be utilized as the high strength yarn in accordance with the present disclosure, and methods of forming the same, is discussed in U.S. Pat. No. 7,582,576 the entire content of which is incorporated herein by reference. In alternate embodiments, the weight ratio between the sheath and the core is about 1:5.

High strength yarns may foam the entire peripheral portion of the mesh or the high strength yarns may be intermingled with primary yarns of the central portion which extend into and/or throughout the peripheral portion of the mesh. It should be understood that the high strength yarns may be intermingled with the primary yarns in any of a variety of ways, such as commingling, interblending, interlacing, and interweaving the yarns via knitting, weaving, sewing, embroidering, among other techniques within the purview of those skilled in the art. Exemplary embodiments of different configurations are described below.

Figure 5:
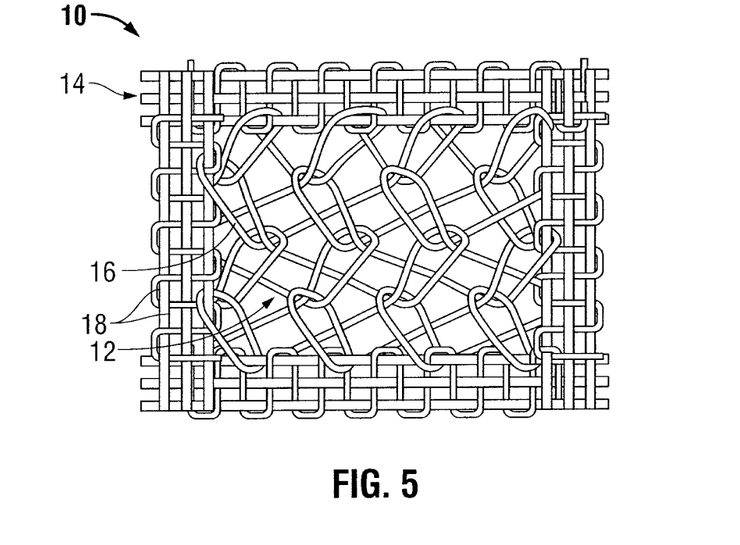
FIG. 5 is a schematic illustration of an embodiment of a surgical mesh in accordance with the present disclosure.

Turning now to FIG. 5, an embodiment of a surgical implant in accordance with the present disclosure is shown. Mesh 10 includes a central portion 12 and a peripheral portion 14 extending radially outward from the central portion 12. Yarns 16 are warp-knitted to form the central portion 12. Peripheral portion 14 is composed solely of high strength yarns 18 which are welt knitted around central portion 12.

Figure 6:
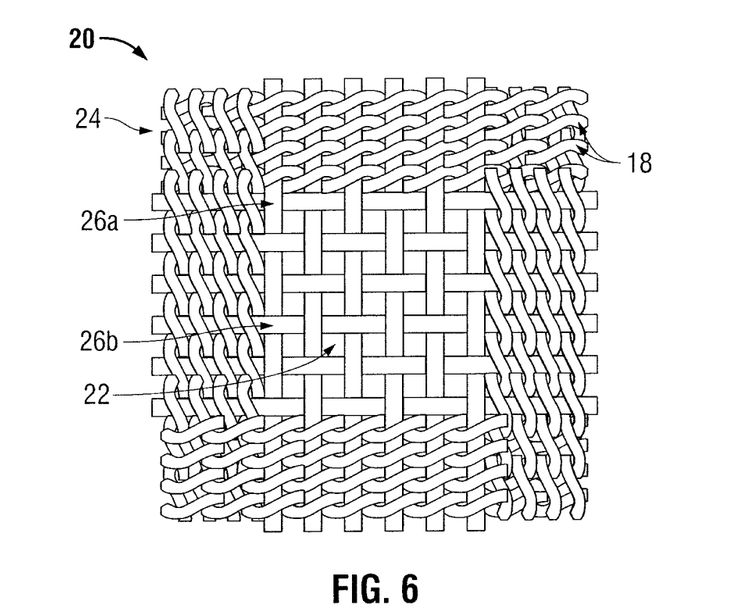
FIG. 6 is a schematic illustration of another embodiment of a surgical mesh in accordance with the present disclosure.

FIG. 6 illustrates an embodiment of a surgical implant in which the high strength yarns are interwoven with the primary yarns of the mesh. Mesh 20 includes central portion 22 and peripheral portion 24 extending around the perimeter of the central portion 22. Two sets of yarns 26a and 26b are woven to form central portion 22. Peripheral portion 24 includes high strength yarns 18 which are woven through primary yarns 26a and 26b.

Figure 7:
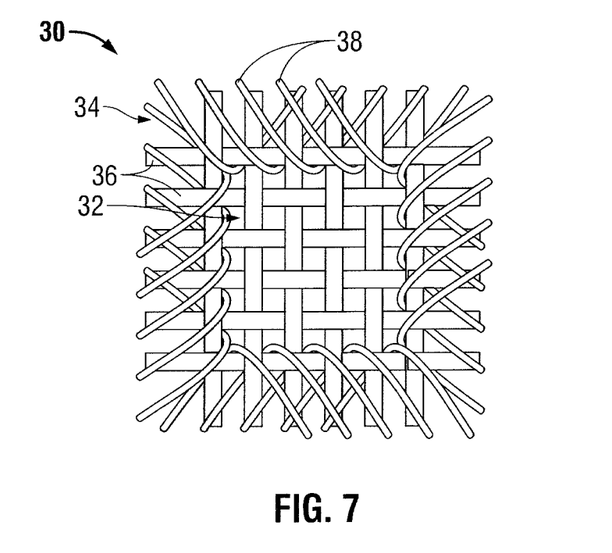
FIG. 7 is a schematic illustration of yet another embodiment of a surgical mesh in accordance with the present disclosure.
Figure 8:
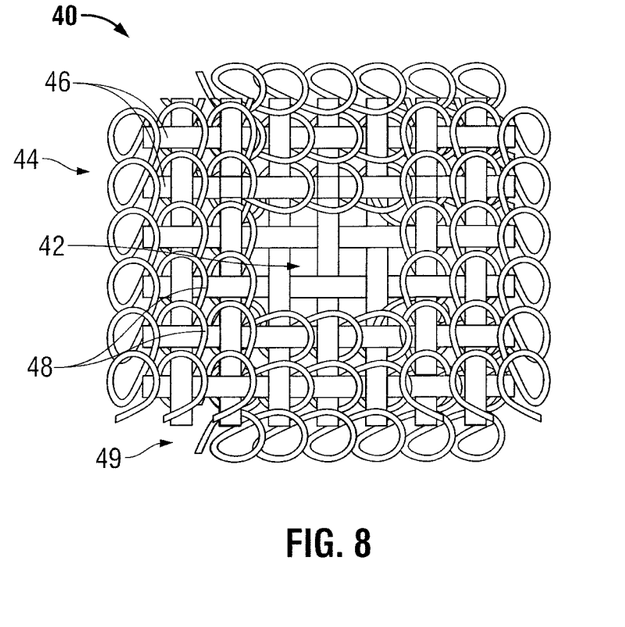
FIG. 8 is a schematic illustration of another embodiment of a surgical mesh in accordance with the present disclosure.

FIGS. 7 and 8 illustrate embodiments of surgical implants in which the high strength yarns are intermingled with the primary yarns of the mesh. As illustrated in FIG. 7, yarns 36 of the central portion 32 extend into peripheral portion 34. High strength yarns 38 are interlaced through yarns 36 in the peripheral portion 34 of the mesh 30. FIG. 8 illustrates yarns 46 of the central portion 42 extending partially into peripheral portion 44 of mesh 40. High strength yarns 48 are sewn around primary yarns 46 in the peripheral portion 44 of mesh 40 and extend outwardly to form a terminal edge 49 of high strength yarn 38 around mesh 40.

Figure 9:
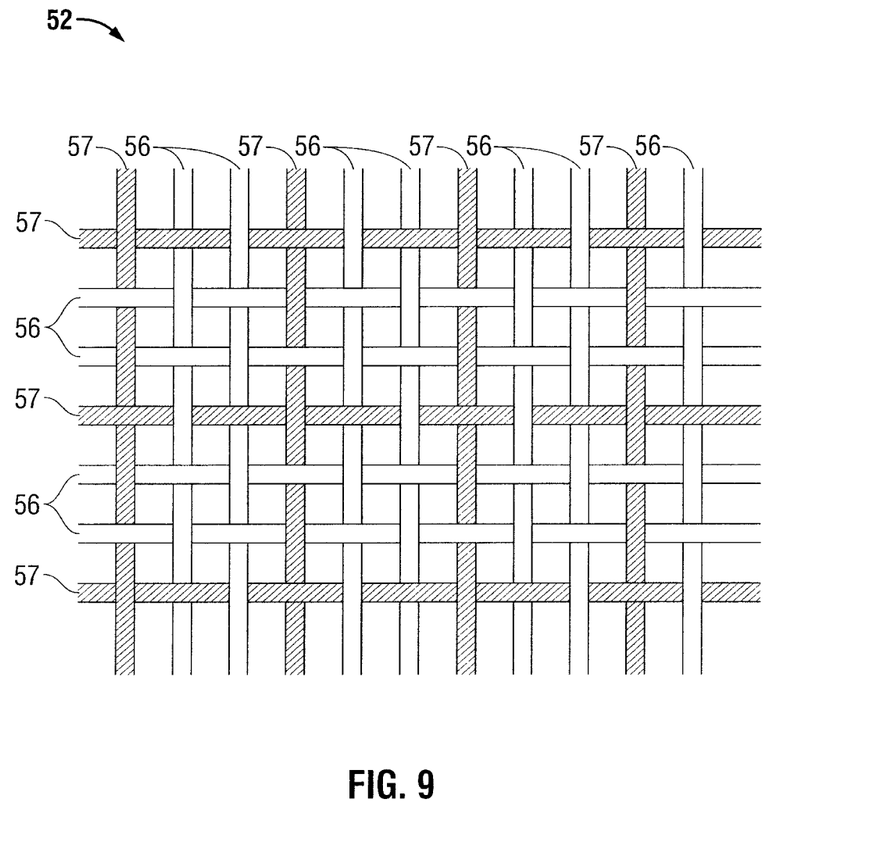
FIG. 9 is a schematic illustration of an embodiment of a central portion of a surgical mesh in accordance with the present disclosure.

FIG. 9 illustrates an embodiment of a central portion 52 of a mesh including both primary yarns 56 and high strength yarns 57 woven to form the central portion 52. Peripheral portion (not shown) includes high strength yarns in any configuration such that the tensile strength of the peripheral portion is greater than the tensile strength of the central portion as described above. It is envisioned that any number of primary yarns 56 and high strength yarns 57, in various arrangements and patterns, may be used to for in the central portion 52 of the mesh while maintaining the relative tensile strengths of the central portion to the peripheral portion.

In general, it should be understood that the implants of the present disclosure are not limited to those illustrated and described herein and alternate meshes may be utilized, including those having a more porous or open pore structure to facilitate tissue in-growth.

A surgical mesh formed from the yarns of the present disclosure may be applied during open surgery. During open surgery, the rigidity of the surgical mesh will allow for ease of handling by the surgeon. In embodiments utilizing absorbable polymers, the absorbable fiber or sheath may dissolve following application and attachment of the mesh to tissue, leaving behind a sufficiently strong mesh needed to maintain the long term integrity of the hernia repair. The remaining mesh will be flexible, forming to the fascial wall. The mesh may also be used, in embodiments, to prevent and/or reduce adhesions which may otherwise occur between a mesh and tissue.

Alternatively, the surgical mesh may be applied during minimally invasive surgery. Laparoscopic surgical procedures are minimally invasive procedures in which operations are carried out within the body by using elongated deployment devices, inserted through small entrance openings in the body. The initial opening in the body tissue to allow passage of the endoscopic or laparoscopic devices to the interior of the body may be a natural passageway of the body, or it can be created by a tissue piercing device, such as a trocar. During laparoscopic procedures, narrow punctures or incisions may be made, thereby minimizing trauma to the body cavity and reducing patient recovery time.

Laparoscopic deployment devices may be used for transferring a mesh into a body cavity. Such devices are within the purview of those skilled in the art and include, for example, the devices disclosed in U.S. Patent Application Publication Nos. 2006/0229640, 2006/0200170, and/or 2006/0200169, the entire disclosures of each of which are incorporated herein by reference.

A mesh according to the present disclosure can be inserted through a small incision (e.g., from about 1 cm to about 2 cm in length) or tissue puncture with the use of a laparoscopic deployment device, such as a needle or trocar. The mesh may be rolled or folded so as to fit within the device for transfer into the body cavity. In embodiments utilizing an absorbable sheath, the absorbable sheath may provide sufficient stiffness to the mesh upon exiting the transfer device, to partially or completely re-open the rolled or folded mesh into its original geometric shape.

In embodiments utilizing an absorbable sheath, the sheath of the bi-component fibers provides the surgical implant with characteristics required for surgical handling. After insertion in the body, the sheath polymer of the bi-component fiber may be absorbed by the body leaving behind the reduced mass of the core polymer of the mesh, which may result in a softer, more compliant mesh.

The high strength yarns of the mesh of the present disclosure provide the implant with suitable characteristic required for fastening the mesh to tissue and minimize or eliminate the propagation of tears within the primary yarns of the mesh. By incorporating high strength yarns into the structure of the mesh, such as through the entire peripheral portion or intermixed therethrough, tearing of the mesh during fixation with surgical fasteners may be reduced as the high strength yarns have the requisite strength to mitigate tearing which may spread from the puncture sites of the fasteners, as well as tears formed by the forces exerted on the mesh upon body movement. Moreover, tear propagation in the lower strength central portion of the mesh may be localized by the high strength yarns of the peripheral portion.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. Various modifications and variations of the polymers utilized in the mesh, as well as methods of forming the central and peripheral portions, interconnecting the central and peripheral portions of the mesh, and incorporating the high strength yarns into the peripheral portion will be apparent to those skilled in the art from the foregoing detailed description. Such modifications and variations are intended to come within the scope and spirit of the claims appended hereto.

What is claimed is:

1. An implant comprising:
   a central portion composed of at least two yarns including at least one primary yarn and at least one high strength yarn interconnected to form openings therein; and
   a peripheral portion extending around the central portion, the peripheral portion formed solely from at least one high strength yarn interconnected to form openings therein.

2. The implant according to claim 1, wherein the at least two yarns of the central portion are interconnected via one of knitting, weaving, and combinations thereof.

3. The implant according to claim 1, wherein the at least one high strength yarn of the peripheral portion has a tensile strength of at least 1 Gpa.

4. The implant according to claim 1, wherein the at least one high strength yarn of the peripheral portion has a tensile strength that is at least 2 times stronger than that of the at least one primary yarn of the central portion.

5. The implant according to claim 1, wherein the at least one high strength yarn of the peripheral portion has a tensile strength that is at least 5 times stronger than that of the at least one primary yarn of the central portion.

6. The implant according to claim 1, wherein the at least one high strength yarn of the peripheral portion has a tensile strength that is about 10 times stronger than that of the at least one primary yarn of the central portion.

7. The implant according to claim 1, wherein one of the at least two yarns of the central portion includes a bi-component fiber.

8. The implant according to claim 7, wherein the bi-component fiber includes a non-absorbable core.

9. The implant according to claim 8, wherein the bi-component fiber includes an absorbable sheath surrounding the non-absorbable core.

10. The implant according to claim 1, wherein the at least one high strength yarn of the peripheral portion is a monofilament yarn.

11. The implant according to claim 1, wherein the at least one high strength yarn of the peripheral portion is a multifilament yarn.

12. The implant according to claim 1, wherein the at least one high strength yarn of the peripheral portion is composed of ultra high molecular weight polyethylene.

13. The implant according to claim 1, wherein the at least one high strength yarn of the peripheral portion is composed of high molecular weight polyethylene terephthalate.

14. The implant according to claim 1, wherein the at least one high strength yarn of the peripheral portion includes a bi-component fiber.

15. The implant according to claim 14, wherein the bi-component fiber includes a non-absorbable core.

16. The implant according to claim 15, wherein the bi-component fiber includes a non-absorbable sheath surrounding the non-absorbable core.

17. The implant according to claim 15, wherein the non-absorbable core is ultra high molecular weight polyethylene.

18. The implant according to claim 1, wherein the peripheral portion has a tensile strength that is at least 50% greater than a tensile strength of the central portion.

19. The implant according to claim 18, wherein the tensile strength of the peripheral portion is about 100% greater than the tensile strength of the central portion.

20. The implant according to claim 18, wherein the tensile strength of the peripheral portion is about 200% greater than the tensile strength of the central portion.

21. The implant according to claim 1, wherein the central portion and the peripheral portion are formed of separate yarns, the at least one high strength yarn of the peripheral portion being interconnected in a different way than the at least two yarns of the central portion.

22. The implant according to claim 21, wherein the at least two yarns of the central portion are warp knitted.

23. The implant according to claim 22, wherein the at least one high strength yarn of the peripheral portion is welt knitted.

* * * * *